(12) United States Patent
Umekawa

(10) Patent No.: US 9,089,295 B2
(45) Date of Patent: Jul. 28, 2015

(54) OPHTHALMIC APPARATUS AND STORAGE MEDIUM

(75) Inventor: Kazuaki Umekawa, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 686 days.

(21) Appl. No.: 13/399,166

(22) Filed: Feb. 17, 2012

(65) Prior Publication Data

US 2012/0220850 A1 Aug. 30, 2012

(30) Foreign Application Priority Data

Feb. 25, 2011 (JP) ................................. 2011-040843

(51) Int. Cl.
*A61B 3/16* (2006.01)
*A61B 3/00* (2006.01)

(52) U.S. Cl.
CPC ............... *A61B 3/165* (2013.01); *A61B 3/0041* (2013.01); *A61B 3/16* (2013.01)

(58) Field of Classification Search
CPC .............. A61B 3/10; A61B 3/12; A61B 3/16; A61B 3/117; A61B 3/165; A61B 3/1005; A61B 3/004; A61B 5/14555; A61B 5/68211
USPC ......................................... 600/399–401, 405
See application file for complete search history.

(56) References Cited

U.S. PATENT DOCUMENTS

| 3,585,849 | A | 6/1971 | Grolman |
| 5,940,165 | A | 8/1999 | Isogai et al. |
| 6,419,631 | B1 * | 7/2002 | Luce .............................. 600/401 |
| 7,153,266 | B2 | 12/2006 | Uchida |
| 7,235,051 | B2 * | 6/2007 | Iwanaga ........................ 600/401 |
| 7,553,282 | B2 * | 6/2009 | Masaki .......................... 600/398 |
| 8,092,019 | B2 * | 1/2012 | Miwa ............................. 351/205 |
| 8,545,404 | B2 * | 10/2013 | Ishii et al. .................... 600/401 |
| 2004/0054277 | A1 | 3/2004 | Uchida |

FOREIGN PATENT DOCUMENTS

| JP | 10-216088 A | 8/1998 |
| JP | 2004-105368 A | 4/2004 |
| JP | 3649839 B2 | 5/2005 |
| JP | 3885015 B2 | 2/2007 |

* cited by examiner

*Primary Examiner* — Max Hindenburg
(74) *Attorney, Agent, or Firm* — Fitzpatrick, Cella, Harper & Scinto

(57) ABSTRACT

An ophthalmic apparatus comprises an imaging unit configured to capture an anterior eye part image of an eye to be examined, a measuring unit configured to measure unique information of the eye, a calculation unit configured to calculate variations of a plurality of pieces of unique information measured by the measuring unit, and a display control unit configured to cause a display unit to display a plurality of anterior eye part images respectively corresponding to the plurality of pieces of unique information when variations calculated by the calculation unit satisfy a predetermined condition.

20 Claims, 8 Drawing Sheets

F I G. 4
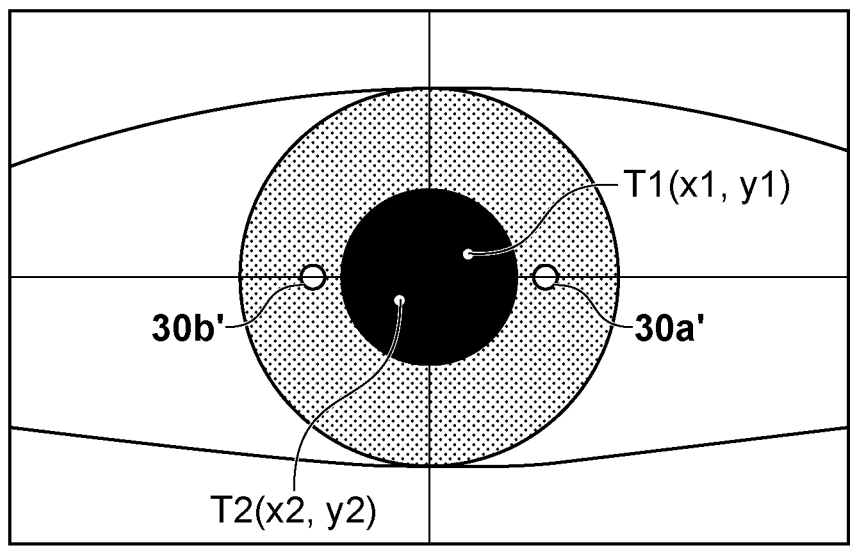

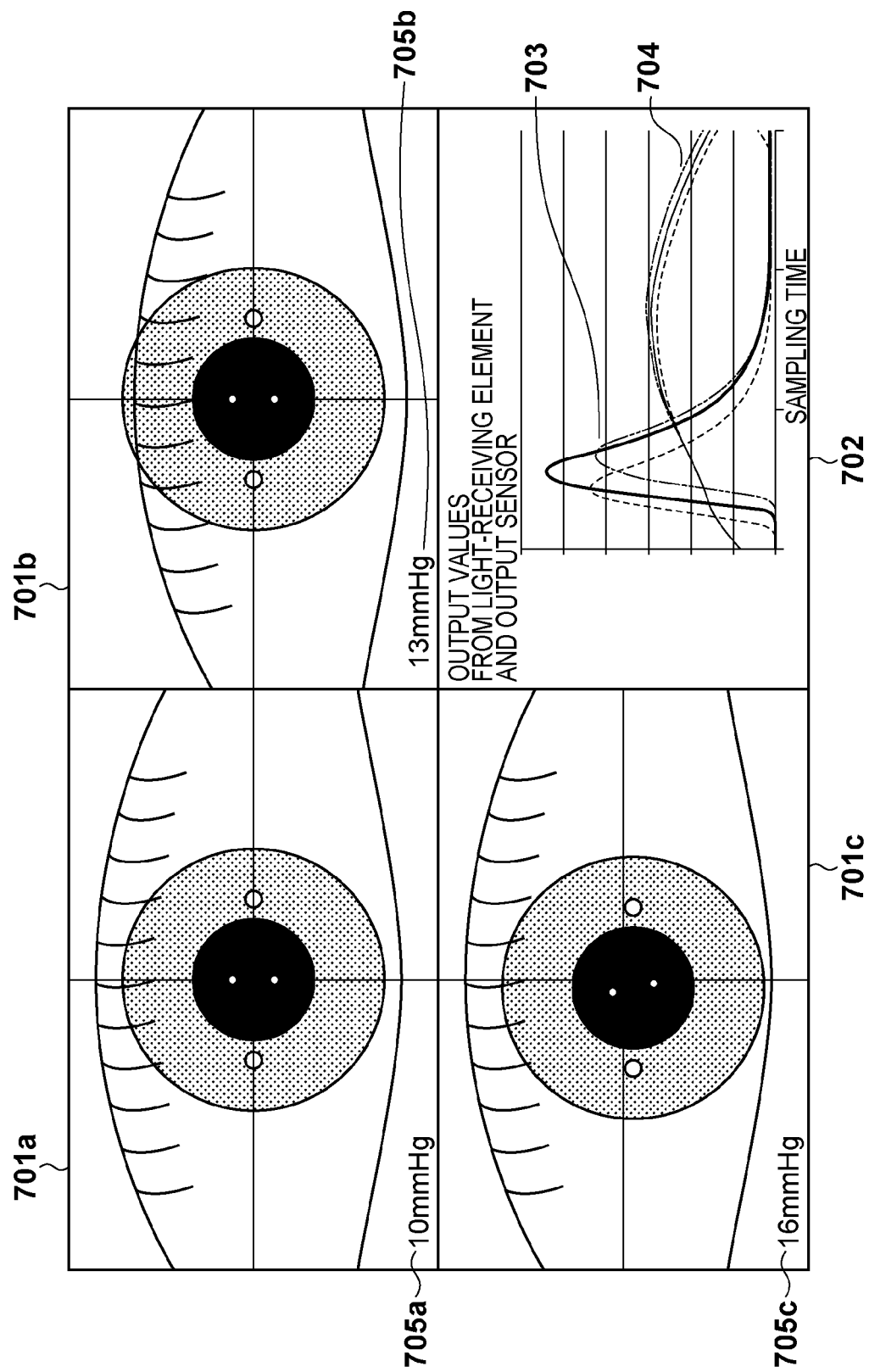

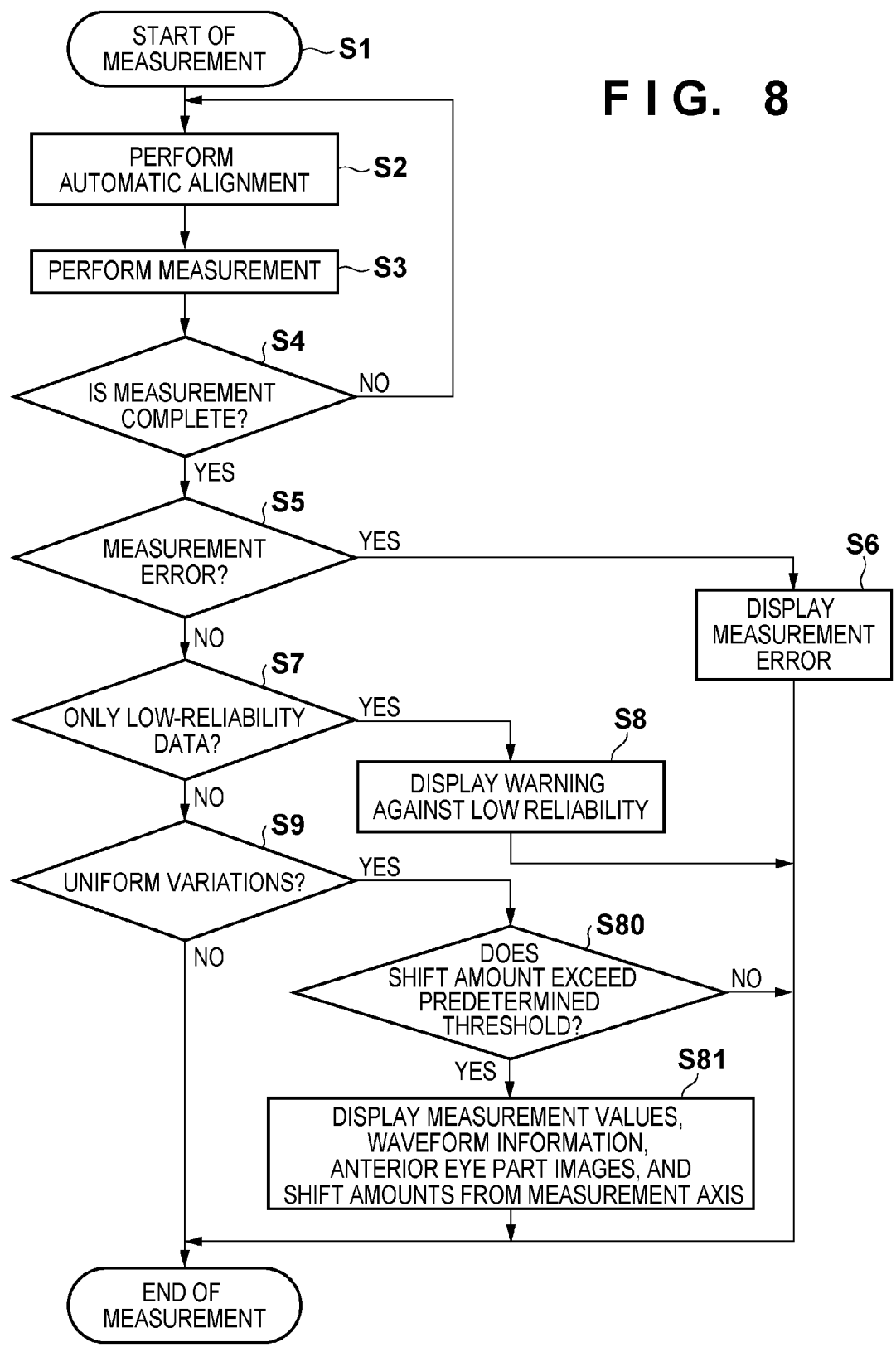

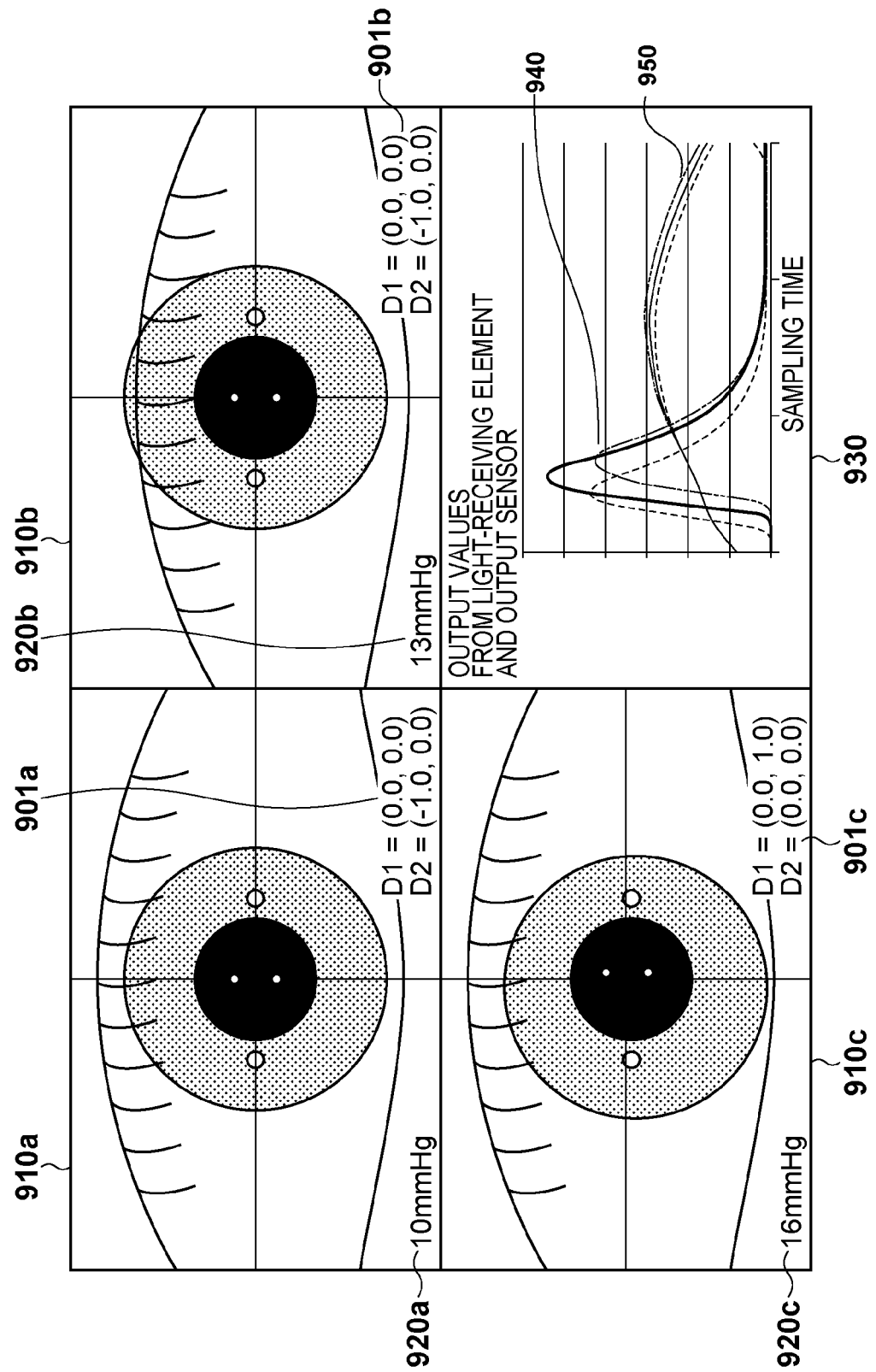

OPHTHALMIC APPARATUS AND STORAGE MEDIUM

BACKGROUND OF THE INVENTION

1. Field of the Invention

The present invention relates to an ophthalmic apparatus and a storage medium.

2. Description of the Related Art

Non-contact tonometers are typified by the air blowing type tonometer disclosed in U.S. Pat. No. 3,585,849 developed by Bernard Grolman. This tonometer is designed to optically detect the applanation of the cornea of an eye to be examined by blowing air against the cornea from a nozzle 11 mm away from the cornea and calculate an eye pressure value by calibrating the time taken for the applanation using a Goldmann contact tonometer. The eye to be examined does not always remain still, and it is sometimes impossible to obtain an accurate measurement value due to the influences of the fixation disparity immediately before air blowing and eyelashes. According to conventional techniques, a degree of reliability is added to a measurement value based on the analysis information of a corneal deformation signal, or a standard value is calculated by statistically processing measurement values corresponding to a plurality of times of measurement, thereby allowing the examiner to select an accurate measurement value.

Fixation disparity immediately before air blowing, the eyelid, and the eyelashes may lead to inability to detect a corneal deformation signal to cause a measurement error. This makes it necessary to perform measurement again. In some cases, when a measurement error has occurred, the examiner cannot distinguish whether he/she could not perform measurement due to the movement of the eye to be examined or due to blinking of the eye. As a conventional technique, there is known the non-contact tonometer disclosed in Japanese Patent No. 3885015 (patent literature 2) which captures an anterior eye part image immediately before air blowing upon observation of the eye to be examined, and stores the captured image. This invention is configured to store an anterior eye part image immediately before air blowing and display a still image upon detection of a corneal reflection bright spot projected on the cornea of the eye to be examined due to a measurement error to check the influences of the eyelid and eyelashes.

When obtaining average data by performing measurement a plurality of times, the examiner needs to determine whether to finish examination, by counting the number of times of measurement or checking displayed measurement values, thus requiring troublesome operation. As a conventional technique, there is known the ophthalmic apparatus disclosed in Japanese Patent No. 3649839 (patent literature 3) which continues measurement until a valid measurement value is obtained. This invention is configured to inform the examiner when a measurement error has consecutively occurred a predetermined number of times, temporarily suspend the completion of alignment, start measurement after alignment is completed again, and continue measurement until a valid measurement value is obtained, thereby reducing the operation load on the examiner.

In some cases, however, measurement values uniformly vary regardless of achieving high reliability after a plurality of times of measurement. This is because, although corneal deformation signals only slightly differ in shape, the timings of the detection of the maximum values of the corneal deformation signals differ due to the influences of the slight fixation disparity, eyelid, or eyelashes. The examiner cannot determine which measurement value he/she should select, because of the high reliability of each measurement value.

According to patent literature 2 described above, although an anterior eye part image immediately before each measurement is stored, this technique is effective for only a measurement error. That is, when measurement is properly performed, the examiner cannot check fixation disparity. Patent literature 3 describes that a variation in measurement value is set as a measurement end condition, and measurement is continued until the standard deviation from an average value falls within a predetermined range. When using a non-contact tonometer, in particular, blowing air against the eye to be examined becomes burdensome to the object.

SUMMARY OF THE INVENTION

The present invention has been made to solve the problems in the conventional techniques described above, and provides an ophthalmic apparatus which can reduce burden on an object by allowing an examiner to select valid unique information when pieces of unique information measured by a plurality of times of measurement vary.

According to one aspect of the present invention, there is provided an ophthalmic apparatus comprising: an imaging unit configured to capture an anterior eye part image of an eye to be examined; a measuring unit configured to measure unique information of the eye; a calculation unit configured to calculate variations of a plurality of pieces of unique information measured by the measuring unit; and a display control unit configured to cause a display unit to display a plurality of anterior eye part images respectively corresponding to the plurality of pieces of unique information when variations calculated by the calculation unit satisfy a predetermined condition.

According to the present invention, even if pieces of unique information measured by a plurality of times of measurement vary, the examiner can select valid unique information. This can reduce the burden on the object. For example, when pieces of unique information measured by a plurality of times of measurement vary, displaying an anterior eye part image immediately before each measurement allows the examiner to select valid unique information by determining the states of the fixation disparity, eyelid, and eyelashes. In addition, since this technique reduces the need to perform re-measurement, it is possible to reduce the burden on the object.

Further features of the present invention will become apparent from the following description of exemplary embodiments (with reference to the attached drawings).

BRIEF DESCRIPTION OF THE DRAWINGS

FIG. 4 is a view exemplifying an anterior eye part image of the eye to be examined;

FIG. 7 is a view showing an example of the display of the measurement result obtained by the non-contact tonometer according to the first embodiment;

FIG. 8 is a flowchart for explaining a procedure for measurement in a non-contact tonometer according to the second embodiment; and FIG. 9 is a view showing an example of the display of the measurement result obtained by the non-contact tonometer according to the second embodiment.

DESCRIPTION OF THE EMBODIMENTS

Figure 1:
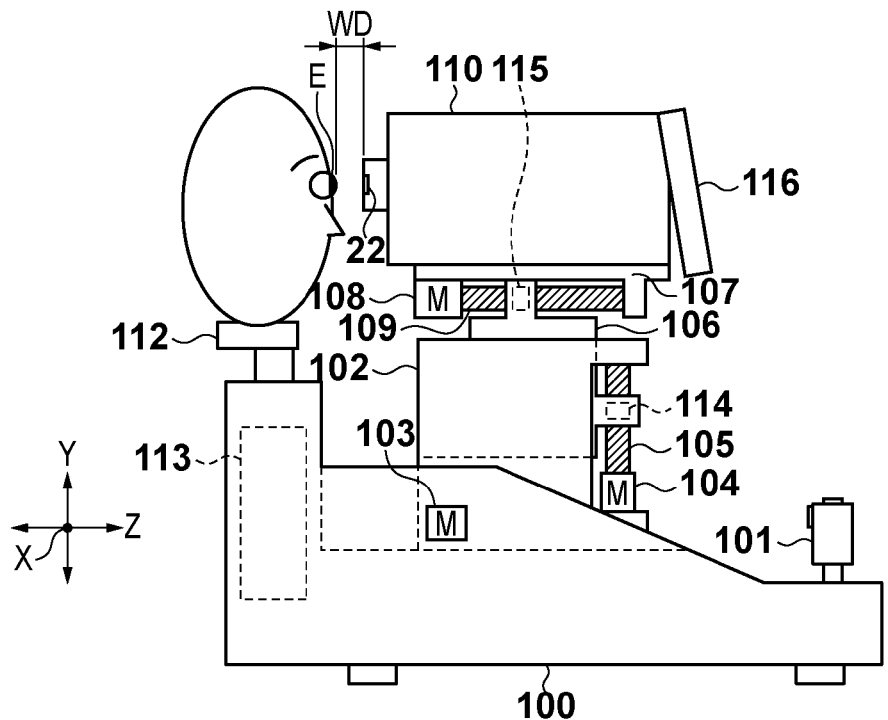
FIG. 1 is a view showing the schematic arrangement of a non-contact tonometer according to an embodiment.

The schematic arrangement of an ophthalmic apparatus according to an embodiment of the present invention will be described with reference to FIG. 1. The ophthalmic apparatus includes, for example, a non-contact tonometer, eye refractive power apparatus, corneal shape measuring apparatus, OCT, and corneal thickness measuring apparatus as apparatuses which need to perform alignment for the eye to be examined, and determine the reliability of measurement data after the completion of alignment. This embodiment will exemplify a non-contact tonometer as an ophthalmic apparatus.

A frame 102 can move in the leftward/rightward direction (to be referred to as the X-axis direction hereinafter: the direction perpendicular to the drawing surface) relative to a base 100. A driving mechanism in the X-axis direction includes an X-axis motor 103 fixed on the base 100, a feed screw (not shown) coupled to the output shaft of the motor, and a nut (not shown) which is fixed to the frame 102 and is movable on the feed screw in the X-axis direction. The X-axis motor 103 rotates to move the frame 102 in the X-axis direction through the feed screw and the nut.

A frame 106 can move in the upward/downward direction (to be referred to as the Y-axis direction hereinafter) relative to the frame 102. A driving mechanism in the Y-axis direction includes a Y-axis motor 104 fixed on the frame 102, a feed screw 105 coupled to the output shaft of the motor, and a nut 114 which is fixed to the frame 106 and is movable on the feed screw in the Y-axis direction. The Y-axis motor 104 rotates to move the frame 106 in the Y-axis direction through the feed screw 105 and the nut 114.

A frame 107 can move in the forward/backward direction (to be referred to as the Z-axis direction hereinafter) relative to the frame 106. A driving mechanism in the Z-axis direction includes a Z-axis motor 108 fixed on the frame 107, a feed screw 109 coupled to the output shaft of the motor, and a nut 115 which is fixed to the frame 106 and is movable on the feed screw in the Z-axis direction. The Z-axis motor 108 rotates to move the frame 107 in the Z-axis direction through the feed screw 109 and the nut 115.

A measuring unit 110 for measurement is fixed on the frame 107. A nozzle 22 for discharging air necessary for eye pressure measurement is provided on the object-side end portion of the measuring unit 110. An LCD monitor 116 as a display member for the observation of an eye E to be examined is provided on the examiner-side end portion of the measuring unit 110.

The base 100 is provided with a joystick 101 as an operation member for positioning the measuring unit 110 to the eye E. In eye pressure measurement, the object rests his/her chin on a chin rest 112, and presses his/her forehead against the forehead rest portion of a face rest frame (not shown) fixed on the base 100, thereby fixing the position of the eye to be examined. The chin rest 112 can be adjusted in the Y-axis direction by a chin rest motor 113 in accordance with the size of the face of the object.

Figure 2:
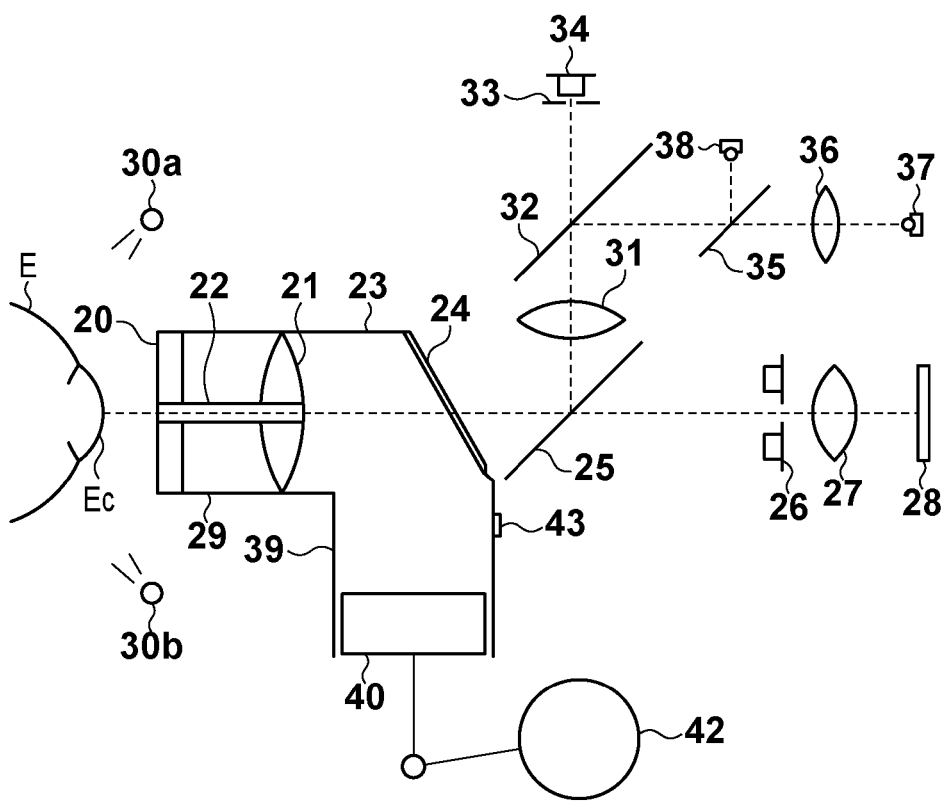
FIG. 2 is a view for explaining the arrangement of an optical system in a measuring unit.

The arrangement of an optical system in the measuring unit 110 will be described with reference to FIG. 2. A plane parallel glass 20 is disposed to face a cornea Ec of the eye E. An objective lens 21 is disposed behind the plane parallel glass 20. The nozzle 22 is disposed on the center axis of the objective lens 21. One end of the nozzle 22 is open to the cornea Ec side of the eye E. The other end of the nozzle 22 is open to an air chamber 23 side. An air chamber 23, an observation window 24, a dichroic mirror 25, a prism stop 26, an imaging lens 27, and a CCD 28 are arranged behind the objective lens 21. They form the light-receiving optical path and alignment detection optical path of an observation optical system for the eye E. An objective lens barrel 29 supports the plane parallel glass 20 and an objective lens 21. Extraocular illumination light sources 30a and 30b for illuminating the eye E are arranged outside the objective lens barrel 29. For the sake of descriptive convenience, the extraocular illumination light sources 30a and 30b are shown on the upper and lower portions of FIG. 2. In practice, however, they are arranged in the vertical direction with respect to the drawing surface so as to face the optical axis.

A relay lens 31, a half mirror 32, an aperture 33, and a light-receiving element 34 are arranged in the reflecting direction of the dichroic mirror 25. An aperture 33 is located such that the position of the aperture 33 is conjugate to a cornea reflection image of a measurement light source 37 (to be described later) when the cornea Ec deforms in a predetermined shape, thus forming a detection optical system which detects a cornea reflection image (corneal deformation signal) when the cornea Ec deforms in the visual axis direction together with the light-receiving element 34.

The relay lens 31 is designed to form a cornea reflection image having almost the same size as that of the aperture 33 when the cornea Ec deforms in the predetermined shape. A half mirror 35, a projection lens 36, and the measurement light source 37 formed from a near-infrared LED having an invisible wavelength used for both measurement and alignment for the eye E are arranged in the incident direction of the half mirror 32. A vision fixation light source 38 formed from an LED for the vision fixation of the object is disposed in the incident direction of the half mirror 35.

In the air chamber 23, a piston 40 is fitted in a cylinder 39 forming part of the air chamber 23. A solenoid 42 drives the piston 40. Note that a pressure sensor 43 for monitoring an internal pressure is disposed in the air chamber 23.

Figure 3:
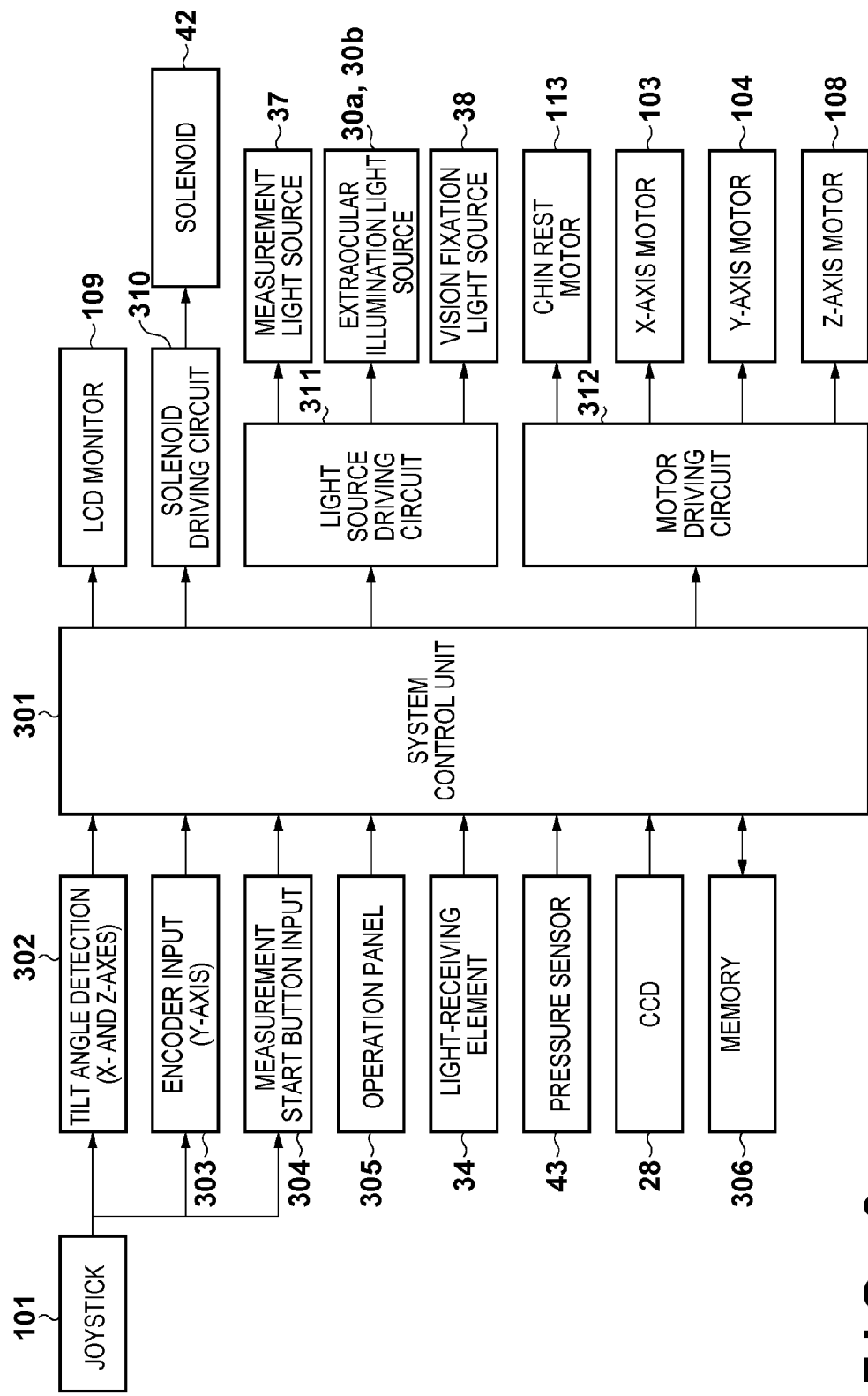
FIG. 3 is a block diagram showing the system arrangement of a non-contact tonometer.

The system arrangement of a non-contact tonometer according to this embodiment of the present invention will be described with reference to the block diagram of FIG. 3. A system control unit 301 controls the overall non-contact tonometer. The system control unit 301 includes a program storage unit, a data storage unit which stores data for correcting the measured eye pressure value (to be referred to as the measurement value hereinafter) of the eye to be examined, an input/output control unit which controls input/output operation with various kinds of devices, and an arithmetic processing unit which arithmetically processes the data obtained from the devices.

The joystick 101 inputs operation commands to the system control unit 301 to perform the operation of positioning the measuring unit 110 to the eye E and start measurement. The system control unit 301 receives a tilt angle detection result 302 obtained when the joystick 101 tilts in the forward/backward direction, an encoder input 303 obtained when the joystick 101 rotates, and a measurement start button input 304 obtained when the measurement start button is pressed. A print button, a chin rest up/down button, and the like are arranged on an operation panel 305 provided on the base 100. When the examiner performs button input operation, a corresponding signal is notified to the system control unit 301.

A memory 306 stores an anterior eye part image of the eye E captured by the CCD 28. The alignment state between the eye to be examined of the object and the measuring unit 110 is detected by extracting a pupil image and cornea reflection image of the eye E from the image stored in the memory 306. When the detection result is input to the system control unit 301, alignment operation is executed under the control of the system control unit 301. The system control unit 301 positions the measuring unit 110 to the eye to be examined by controlling the X-axis motor 103, the Y-axis motor 104, and the Z-axis motor 108 via a motor driving circuit 312 based on the alignment state detection result. The LCD monitor 116 displays the anterior eye part image of the eye E captured by the CCD 28, together with an eye pressure measurement value and measurement information representing changes in output values from the light-receiving element 34 and the pressure sensor 43 under the display control of the system control unit 301. The memory 306 stores the corneal deformation signal received by the light-receiving element 34 and the signal obtained by the pressure sensor 43 disposed in the air chamber 23.

The system control unit 301 performs drive control of the solenoid 42 via a solenoid driving circuit 310. The system control unit 301 performs drive control of the X-axis motor 103, Y-axis motor 104, Z-axis motor 108, and chin rest motor 113 via the motor driving circuit 312. The system control unit 301 controls turning on/off and changing of the light amounts of the measurement light source 37, extraocular illumination light sources 30a and 30b, and vision fixation light source 38 via a light source driving circuit 311.

FIG. 4 shows how an anterior eye part image of the eye to be examined is captured. At the time of alignment, the prism stop 26 divides the cornea bright spot image formed on the cornea Ec into images (T1, T2). The CCD 28 captures the divided index images (T1, T2), together with the eye E illuminated by the extraocular illumination light sources 30a and 30b and bright spot images 30a' and 30b' of the extraocular illumination light sources 30a and 30b. The system control unit 301 performs precise positioning by using coordinates T1 and T2 of the index images captured by the CCD 28. FIG. 4 shows a state in which the center axis of the nozzle 22 and the center of the cornea Ec shift from each other both in the center axis direction of the nozzle 22 and an in-plane direction.

Figure 5A:
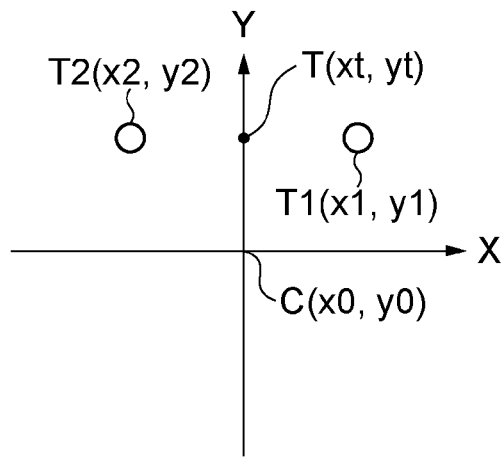
FIGS. 5A to 5D are graphs for explaining an alignment method for a non-contact tonometer.

When performing alignment, the system control unit 301 calculates coordinates T1(x1, y1) and T2(x2, y2) of two index images and center coordinates T(xt, yt) of T1 and T2. Assume that the center coordinates T(xt, yt) coincide with the optical axis of the optical part of the measuring unit 110. Alignment using the coordinates T1 and T2 of the index images will be described with reference to FIGS. 5A to 5D. Note that FIGS. 5A to 5D show the center of the cornea Ec as an intersection point C(x0, y0) of the x- and y-coordinates. As shown in FIG. 5A, when the center axis of the nozzle 22 and the center of the cornea Ec shift from each other in the upward/downward direction (y direction), an x-coordinate value (x0) of a cornea center C(x0, y0) coincides with an x-coordinate value (xt) of the center coordinates T(xt, yt). However, a y-coordinate value (y0) of the cornea center C differs from a y-coordinate value (yt) of the center coordinates T. For alignment in this case, the system control unit 301 performs control to drive the Y-axis motor 104 to move the measuring unit 110 in the upward/downward direction (y direction) so as to make the y-coordinate value (y0) of the cornea center C coincide with the y-coordinate value (yt) of the center coordinates T.

Figure 5B:
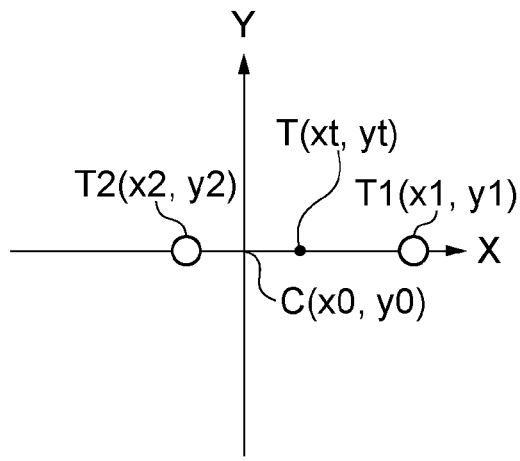

If the center of the nozzle and the cornea center shift from each other in the leftward/rightward direction (x direction), the x-coordinate value (x0) of the cornea center C differs from the x-coordinate value (xt) of the center coordinates T, as shown in FIG. 5B. In this case, the system control unit 301 performs control to drive the X-axis motor 103 to move the measuring unit 110 in the leftward/rightward direction (x direction) so as to make the x-coordinate value (x0) of the cornea center C coincide with the x-coordinate value (xt) of the center coordinates T.

Figure 5C:
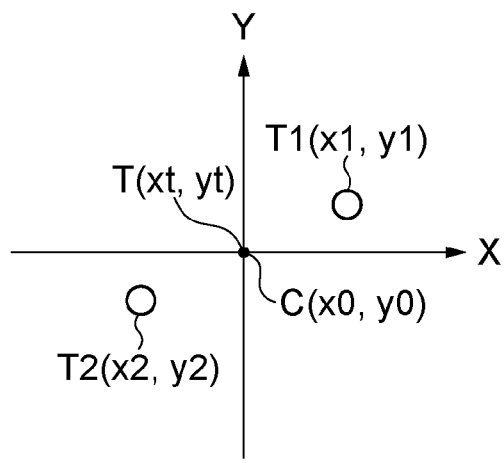
Figure 5D:
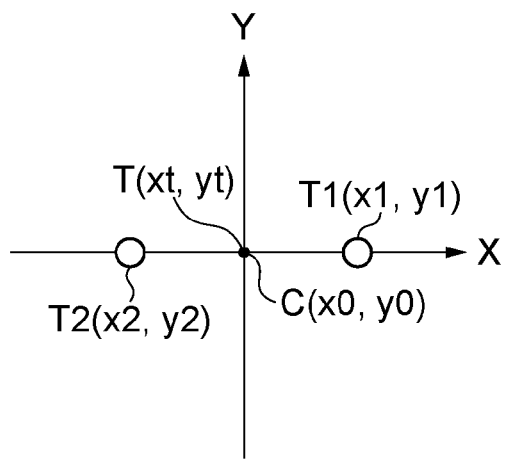

If the center of the nozzle 22 and the center of the cornea Ec shift from each other in the operation distance direction (z direction), the center coordinates T(xt, yt) coincide with the cornea center C(x0, y0), as shown in FIG. 5C, but both the x-coordinate values x1 and x2 and the y-coordinate values y1 and y2 of the two index images differ from each other. In this case, for alignment, the system control unit 301 drives the Z-axis motor 108 to move the housing of the cylinder 39 in the center axis direction (z direction) of the nozzle 22 so as to make the x-coordinate values x1 and x2 and y-coordinate values y1 and y2 of the two index images coincide with each other. Upon completion of the alignment, as shown in FIG. 5D, the coordinates T1 and T2 of the two index images are located side by side on the X-axis at equidistances from the center coordinates T of the cornea Ec, and the center coordinates T(xt, yt) between the coordinates T1 and T2 of the index images coincide with the cornea center C(x0, y0).

(Measurement of Unique Information)

Measurement of measurement values (unique information) measured by the ophthalmic apparatus will be described. The unique information measured by the respective apparatuses included by the above ophthalmic apparatus includes, for example, an eye pressure, eye refractive power, corneal shape, and corneal thickness. The following will exemplify eye pressure measurement using a non-contact tonometer. After performing alignment state detection, aligning operation of positioning the measuring unit 110 to the eye to be examined, and completing positioning by aligning operation, the system control unit 301 performs eye pressure measurement by controlling the operation of the non-contact tonometer. The system control unit 301 drives the solenoid 42 via the solenoid driving circuit 310. Driving the solenoid 42 will compress the air in the air chamber 23 using the piston 40 pushed upward by the solenoid 42, thereby blowing air in the form of a pulse from the opening portion of the nozzle 22 against the cornea Ec of the eye E. The system control unit 301 receives the pressure signal detected by the pressure sensor 43 of the air chamber 23 and a corneal deformation signal from the light-receiving element 34. The system control unit 301 calculates unique information from the peak value of the corneal deformation signal (light reception signal) input from the light-receiving element 34 and a pressure signal corresponding to the peak value input from the pressure sensor 43.

Figure 6:
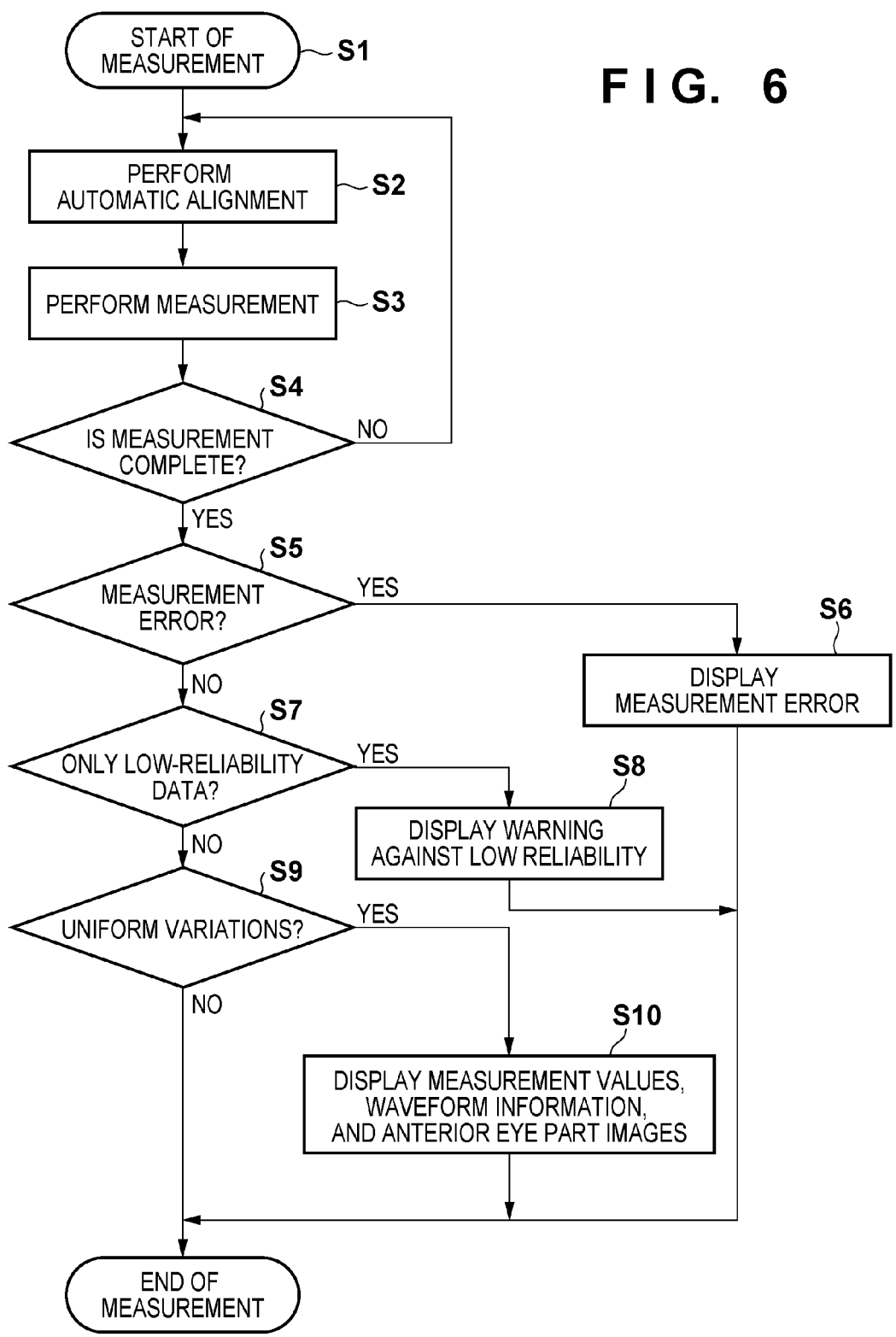
FIG. 6 is a flowchart for explaining a procedure for measurement in a non-contact tonometer according to the first embodiment.

A procedure for measurement in the non-contact tonometer according to the embodiment of the present invention will be described with reference to FIG. 6. This procedure for measurement is executed under the overall control of the system control unit 301. In step S1, the system control unit 301 starts eye pressure measurement. The examiner makes the object rest his/her chin on the chin rest 112, and adjusts the eye to be examined at a predetermined height in the Y-axis direction using the chin rest motor 113. The examiner operates the joystick 101 up to a position at which a cornea reflection image of the eye E depicted on the LCD monitor 116 is displayed, and adjusts the eye to be examined at a predetermined height in the Y-axis direction. When completing the adjustment, the examiner presses the measurement start button.

When the examiner presses the measurement start button, the system control unit 301 starts automatic alignment in step S2. The system control unit 301 extracts a cornea reflection image from the anterior eye part image of the eye E stored in the memory 306, and performs alignment by the alignment method described above with reference to FIGS. 5A to 5D.

Upon completion of the alignment, the process advances to step S3 to execute the tonometry method described above under the control of the system control unit 301. In eye pressure measurement, the system control unit 301 stores, in the memory 306, the corneal deformation signal and pressure signal input to the system control unit 301. In addition, the system control unit 301 captures an anterior eye part image of the eye E before measurement performed by blowing air against the cornea Ec of the eye E, and stores the image in the memory 306.

In step S4, the system control unit 301 determines the completion of measurement consecutively performed a plurality of times. Assume that a condition for determining the completion of measurement is that eye pressure measurement is performed consecutively three times. In this case, if measurement has been performed less than three times (NO in step S4), the process returns to step S2. If the system control unit 301 performs eye pressure measurement again (S3) and completes measurement consecutively three times (YES in step S4), the process advances to step S5. The system control unit 301 stores the anterior eye part image captured before each measurement in the memory 306 in correspondence with measurement information obtained by the measurement.

In step S5, the system control unit 301 determines whether a measurement error has occurred. If the system control unit 301 determines that a measurement error has occurred (YES in step S5), the system control unit 301 displays the measurement error on the LCD monitor 116 (S6), thereby terminating the measurement. If no measurement error has occurred (NO in step S5), the process advances to step S7.

In step S7, the system control unit 301 (first determination unit) determines whether a measurement value (unique information) measured as unique information satisfies a condition as a criterion indicating reliability. The system control unit 301 can determine the reliability of unique information from analysis information of a corneal deformation signal. If, for example, the peak light amount of a corneal deformation signal is smaller than a predetermined threshold, the system control unit 301 determines that the unique information does not satisfy the condition as the criterion indicating reliability. If the waveform of a portion indicating the peak light amount of a corneal deformation signal, other than the peak light amount of the corneal deformation signal, is disturbed beyond a predetermined threshold relative to a waveform as a criterion, the system control unit 301 determines that the unique information does not satisfy the condition as the criterion indicating reliability. In addition, the system control unit 301 performs statistical processing using a plurality of pieces of unique information. If given unique information differs from the average value by a predetermined value or more, the system control unit 301 determines that the reliability is low. Alternatively, the system control unit 301 classifies pieces of unique information which differ from the average value by a predetermined value or more into groups, and then determines that the reliability of a group including a small number of data is low. If the system control unit 301 determines that all the pieces of unique information do not satisfy the criterion indicating reliability (YES in step S7), the process advances to step S8 to make the LCD monitor 116 display a warning against reliability (S8). The system control unit 301 then terminates the measurement. Assume that the system control unit 301 performs eye pressure measurement consecutively three times. In this case, if the system control unit 301 determines that all the pieces of unique information obtained by the three times of eye pressure measurement do not satisfy the criterion indicating reliability, the system control unit 301 displays a warning against reliability. In contrast, if the system control unit 301 determines in step S7 that at least one piece of unique information has high reliability, the process advances to step S9.

In step S9, the system control unit 301 performs statistic processing of all pieces of unique information, and determines from the statistic processing result whether the pieces of unique information measured as unique information uniformly vary. In this embodiment, when unique information differs from the average value by, for example, 3 (mmHg) or more, the system control unit 301 determines that the information has a variation (deviation). Note that the difference from an average value by which it is determined that there is a variation is not limited to 3 (mmHg), and can be set to an arbitrary value by the examiner or the like.

Assume that 10, 13, and 16 (mmHg) are obtained as the results obtained by three times of eye pressure measurement. When calculating the average value of three measurement values (unique information) and deviations of the pieces of unique information from the average value, 10 (mmHg) has a variation (deviation) of −3 (mmHg) from the average value (13 mmHg), and 16 (mmHg) has a variation (deviation) of +3 (mmHg). The system control unit 301 determines whether the pieces of unique information vary (uniformly) such that the number of pieces of unique information with positive deviations from the average value is equal to that of pieces of unique information with negative deviations from the average value. In this case, since the unique information (10 mmHg) having a deviation of −3 from the average value of 13 (mmHg) and the unique information (16 mmHg) having a deviation of +3 from the average value uniformly vary, it is impossible to determine from statistic processing which unique information is low in reliability. Assume that 11, 12, 18, and 19 (mmHg) have been obtained as the results of four times of measurement. In this case, the average value is 15 (mmHg). When classifying pieces of unique information with variations (deviations) within +/−3 mmHg relative to the average values into the first group, the first group includes 12 and 18 (mmHg). When classifying pieces of unique information with variations exceeding +/−3 mmHg relative to the average values into the second group, the second group includes 11 and 19 (mmHg). Although the pieces of unique information are classified into the first and second groups by statistic processing, since the numbers of data in the respective groups are equal to each other (two in each group), it is impossible to determine which group is low in reliability. Assume that 9, 10, and 11 (mmHg) have been obtained as the results of three times of eye pressure measurement. In this case, 9 (mmHg) differs from the average value (10 (mmHg)) by −1 (mmHg), and 11 (mmHg) differs from the average value by +1 (mmHg). Since there are no variations (deviations) equal to or more than 3 (mmHg), the system control unit 301 determines that there is no variation and the pieces of unique information do not uniformly vary.

Upon determining in step S9 that the pieces of unique information measured as unique information do not uniformly vary, the system control unit 301 terminates the measurement. In contrast, if the system control unit 301 determines that the pieces of unique information uniformly vary relative to the average value (YES in step S9), the process advances to step S10.

In step S10, the LCD monitor 116 displays an anterior eye part image immediately before measurement (before the start of measurement), the corneal deformation signal, the waveform of the pressure signal, and the unique information of the eye pressure, stored in the memory 306 in each measurement, under the display control of the system control unit 301. FIG. 7 shows a display example of the results obtained by three times of measurement.

Reference numerals 701a, 701b, and 701c in FIG. 7 denote anterior eye part images captured immediately before the respective measurements. The anterior eye part image 701a indicates a case in which the eyelid is open properly without any fixation disparity. The anterior eye part image 701b indicates a case in which measurement starts immediately before blinking because the eyelid has begun to close although no fixation disparity has occurred. The anterior eye part image 701c indicates a state in which although the eyelid is open properly, fixation disparity or alignment error has occurred. An image 702 is a view representing changes in output values from the light-receiving element 34 and the pressure sensor 43 at sampling time intervals. Output waveforms 703 are the waveforms of output values (corneal deformation signals) in the respective measurements from the light-receiving element 34. Output waveforms 704 indicate the waveforms of output values (pressure signals) in the respective measurements from the pressure sensor 43. Of the output waveforms 703 and 704, the solid lines correspond to the anterior eye part image 701a, the chain double-dashed lines correspond to the anterior eye part image 701b, and the broken lines correspond to the anterior eye part image 701c. The output peak (solid line) of the light-receiving element corresponding to the anterior eye part image 701a corresponding to the state in which the eyelid is open properly without any fixation disparity is higher than the output peaks of the light-receiving elements corresponding to the remaining anterior eye part images 701b and 701c. This indicates that the light reception state is proper. The output response (chain double-dashed line) of the light-receiving element corresponding to the anterior eye part image 701b exhibits a delay in rise time due to the influence of the eyelid or eyelashes, and the corresponding output peak is lower than the output peaks of the light-receiving elements corresponding to the anterior eye part images 701a and 701c. On the other hand, the output (chain double-dashed line) of the pressure sensor corresponding to the anterior eye part image 701b is higher than the outputs of the pressure sensors corresponding to the remaining anterior eye part images 701a and 701c due to the influences of the eyelid and eyelashes. The output peak (broken line) of the light-receiving element corresponding to the anterior eye part image 701c is lower than the output peak (solid line) of the light-receiving element of the anterior eye part image 701a due to the influence of the fixation disparity or alignment error. The output from the pressure sensor corresponding to the anterior eye part image 701c is also lower than the outputs from the pressure sensors corresponding to the remaining anterior eye part images 701a and 701b.

When the variations (deviations) of a plurality of pieces of unique information are uniform relative to the average value of the plurality of pieces of unique information, the system control unit 301 displays, on the LCD monitor 116, a combination of an anterior eye part image and measurement information stored in the memory 306. In this case, the measurement information includes the eye pressure measurement value (for example, 10, 13, and 16 mmHg) obtained by the respective measurements and waveform information indicating time-series changes in output values from the light-receiving element 34 and pressure sensor 43 at sampling time intervals. The anterior eye part image 701a displayed on the screen of the LCD monitor 116 depicts an eye pressure measurement value 705a (10 mmHg). The anterior eye part image 701b depicts an eye pressure measurement value 705b (13 mmHg), and the anterior eye part image 701c depicts an eye pressure measurement value 705c (16 mmHg) (FIG. 7). The information displayed as shown in FIG. 7 allows the examiner to know that he/she should select the eye pressure measurement value 705a (10 mmHg) on the anterior eye part image 701a in the state in which the eyelid is open properly without any fixation disparity. When the examiner selects an anterior eye part image which he/she determines as having the highest reliability on the window in FIG. 7, the system control unit 301 stores the unique information of the selected anterior eye part image as unique information having the highest reliability in the memory 306. If the LCD monitor 116 is a touch panel, the examiner can select an anterior eye part image which he/she determines as having the highest reliability by touching the image. Alternatively, the examiner can select an anterior eye part image which he/she determines as having the highest reliability by moving the cursor to the anterior eye part image on the window by operating an input device such as a mouse. The system control unit 301 adds an identification mark (for example, a circle) onto the window to identify the unique information of the anterior eye part image selected by the examiner as a standard value (representative value) relative to the pieces of unique information of the remaining anterior eye part images. The system control unit 301 sets a reliability coefficient indicating the highest reliability for the selected unique information.

The above embodiment has exemplified the case in which one eye is measured consecutively a plurality of times. Assume that upon measuring the eye pressure of one of the eyes of the object which are the eyes to be examined, the system control unit 301 accepts an operation instruction for consecutively measuring the eye pressure of the other eye to be examined. In this case, the system control unit 301 controls the operation of the non-contact tonometer in the following manner.

When consecutively measuring the left and right eyes, the system control unit 301 measures the right eye as one eye first, and then automatically drives the measuring unit 110 from the right eye to the left eye to automatically measure the left eye as the other eye in a series of operations (full automatic measurement). In such full automatic measurement, when pieces of unique information uniformly vary upon completion of the measurement for the right eye, the system control unit 301 temporarily interrupts the full automatic measurement.

The system control unit 301 then displays an anterior eye part image immediately before measurement on the right eye (before the start of measurement), the corneal deformation signal, the waveform of the pressure signal, and the unique information of eye pressure on the LCD monitor 116 (for example, FIG. 7). Assume that upon accepting the valid unique information input by the examiner, the system control unit 301 accepts one measurement result selected from the measurement results obtained by a plurality of times of measurement, and the examiner presses the measurement start button. In this case, the system control unit 301 resumes the temporarily interrupted full automatic measurement. Upon resuming the full automatic measurement, the system control unit 301 measures the left eye as the other eye. If pieces of unique information uniformly vary, the system control unit 301 displays an anterior eye part image immediately before measurement on the left eye, the corneal deformation signal, the waveform of the pressure signal, and the unique information on the LCD monitor 116 (for example, FIG. 7). Upon accepting the valid unique information input by the examiner, the system control unit 301 terminates the processing.

According to this embodiment, even if pieces of unique information are properly measured without any measurement error by a plurality of times of measurement, and the pieces of unique information uniformly vary, displaying an anterior eye part image immediately before each measurement allows the examiner to determine the states of the fixation disparity, eyelid, and eyelashes and select valid unique information. In addition, since this reduces the need to perform re-measurement, it is possible to reduce the burden on the object.

In addition, according to this embodiment, since the difference from an average value by which it is determined that there is a variation is set to a predetermined value or more, if pieces of unique information uniformly vary but differ little from the average value, an anterior eye part image immediately before each measurement is not displayed. This can avoid an anterior eye part image immediately before each measurement from being displayed more than necessary.

Second Embodiment

The first embodiment has exemplified the arrangement configured to display, on the LCD monitor 116, an anterior eye part image immediately before measurement, a corneal deformation signal, the waveform of a pressure signal, and unique information, based on a condition as a criterion indicating the reliability of unique information, that is, the condition whether pieces of unique information uniformly vary. The second embodiment will exemplify an arrangement configured to add, to the above condition, a condition of whether the shift of a measurement optical axis is a predetermined threshold or more as information for the selection of an eye pressure measurement result. A procedure for measurement in a non-contact tonometer according to the second embodiment of the present invention will be described with reference to FIG. 8.

FIG. 8 shows a measurement procedure obtained by adding, to the measurement procedure described with reference to FIG. 6, the processing step (S80) of determining whether the shift of the measurement optical axis of an anterior eye part image immediately before measurement (before the start of measurement) exceeds a predetermined threshold. A description of processing steps common to those in FIG. 6 will be omitted to avoid redundancy.

If a system control unit 301 determines in step S9 that a plurality of pieces of unique information uniformly vary relative to the average value of the plurality of pieces of unique information (YES in step S9), the process advances to step S80.

In step S80, the system control unit 301 calculates a shift amount relative to the measurement optical axis from an anterior eye part image stored in a memory 306, and compares the shift amount with a threshold. Upon determining that the shift amount falls within the threshold, the system control unit 301 terminates the measurement. If the system control unit 301 (second determination unit) determines that the shift amount exceeds the predetermined threshold (YES in step S80), the process advances to step S81.

In step S81, the system control unit 301 displays, on an LCD monitor 116, an anterior eye part image immediately before measurement (before the start of measurement), an output signal (corneal deformation signal) from the light-receiving element, the waveform of an output signal (corneal deformation signal) from the light-receiving element, the waveform of an output signal (pressure signal) from the pressure sensor, the unique information of an eye pressure, and the shift amount from the measurement optical axis. FIG. 9 shows a display example corresponding to three measurements. The system control unit 301 displays a combination of an anterior eye part image and measurement information stored in the memory 306 on the LCD monitor 116. In this case, measurement information includes information indicating the shift amount from the measurement optical axis, in addition to eye pressure measurement values (for example, 10, 13, and 16 mmHg) and time-series changes in output values from a light-receiving element 34 and a pressure sensor 43 at sampling time intervals.

Reference numeral 910a, 910b, and 910c in FIG. 9 denote anterior eye part images captured immediately before the respective measurements (before the starts of measurements). The anterior eye part images 910a and 910c indicate eyelid open states. The anterior eye part image 910b indicates a case in which measurement starts immediately before blinking because the eyelid has begun to close. An image 930 is a view showing changes in output values from the light-receiving element 34 and pressure sensor 43 at sampling time intervals. Output waveforms 940 are the waveforms of output values (corneal deformation signals) in the respective measurements from the light-receiving element 34. Output waveforms 950 indicate the waveforms of output values (pressure signals) in the respective measurements from the pressure sensor 43. Of the output waveforms 940 and 950, the solid lines correspond to the anterior eye part image 910a, the chain double-dashed lines correspond to the anterior eye part image 910b, and the broken lines correspond to the anterior eye part image 910c.

Reference numerals 901a, 901b, and 901c in FIG. 9 respectively indicate shift amounts D1 and D2 of the measurement optical axes of anterior eye part images immediately before a plurality of times of measurement (before the starts of measurements). Of the shift amounts of the measurement optical axes, the shift amount D1 indicates the shift amount between the cornea center and the measurement optical axis which is calculated from the cornea reflection image projected on the vertex of the cornea. The shift amount D2 indicates the shift amount between the pupil center and the measurement optical axis. With the shift amount 901a of the anterior eye part image 910a, the cornea center coincides with the measurement optical axis (D1), but the pupil center does not coincide with the measurement optical axis (D2). With the shift amount 901b of the anterior eye part image 910b, the cornea center coincides with the measurement optical axis (D1), but the pupil center does not coincide with the measurement optical axis (D2). With the shift amount 901c of the anterior eye part image 910c, the cornea center does not coincide with the measurement optical axis (D1), but the pupil center coincides with the measurement optical axis (D2).

With regard to the anterior eye part images 910a and 910c each indicating an eyelid open state, the shift amounts 901a and 901c are compared with each other to narrow down selection. If there is no shift between the cornea center and the measurement optical axis, blowing compressed air deforms the cornea into a flat state, and hence can obtain a good measurement result. For example, the shift (D1 of 901c) between the cornea center of the anterior eye part image 910c and the measurement optical axis is larger than the shift (D1 of 901a) between the cornea center of the anterior eye part image 910a and the measurement optical axis. This allows the examiner to know that he/she should select the eye pressure measurement value (10 mmHg) of the anterior eye part image 910a as unique information on which the shift between the measurement optical axis and the cornea center is small.

According to this embodiment, even if pieces of unique information are properly measured without any measurement error by a plurality of times of measurement, and the pieces of unique information uniformly vary, displaying an anterior eye part image immediately before each measurement allows the examiner to determine the states of the fixation disparity, eyelid, and eyelashes and select valid unique information. In addition, since this reduces the need to perform re-measurement, it is possible to reduce the burden on the object.

Other Embodiments

The disclosed technique is not limited to the above embodiment, and can be variously modified and executed within the gist of this embodiment.

This embodiment is configured to display a combination of an anterior eye part image and measurement information on the LCD monitor 116 when a plurality of pieces of unique information uniformly vary relative to the average value of the plurality of pieces of unique information. However, the present invention is not limited to this. For example, the system control unit 301 may display only an anterior eye part image on the LCD monitor 116 when a plurality of pieces of unique information uniformly vary relative to the average value of the plurality of pieces of unique information. In this case, based on the states of the anterior eye part images (for example, the states of the eyelid, eyelashes, and alignment), the examiner selects an anterior eye part image determined as having the highest reliability. The system control unit 301 then stores the unique information of the selected anterior eye part image as unique information having the highest reliability in the memory 306.

In this embodiment, the number of times of measurement is three. However, the present invention is not limited to this. It is possible to set the number of times of measurement to an arbitrary number of times.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-040843, filed Feb. 25, 2011, which is hereby incorporated by reference herein in its entirety.

What is claimed is:

1. An ophthalmic apparatus comprising:
    an imaging unit configured to capture an anterior eye part image of an eye to be examined;
    a measuring unit configured to measure unique information of the eye;
    a calculation unit configured to calculate variations of a plurality of pieces of unique information measured by said measuring unit; and
    a display control unit configured to cause a display unit to display a plurality of anterior eye part images respectively corresponding to the plurality of pieces of unique information when variations calculated by said calculation unit satisfy a predetermined condition.

2. The apparatus according to claim 1, wherein said display control unit causes the display unit to further display the plurality of pieces of unique information when the variations calculated by said calculation unit satisfy a predetermined condition.

3. The apparatus according to claim 1, further comprising a determination unit configured to determine whether each of the plurality of pieces of unique information satisfies a condition as a criterion indicating reliability,
    wherein said calculation unit calculates an average value of the plurality of pieces of unique information determined by said determination unit as satisfying the condition, and calculates variations of the plurality of pieces of unique information relative to the average value.

4. The apparatus according to claim 3, wherein when variations of the plurality of pieces of unique information relative to the average value calculated by said calculation unit satisfy the condition, said display control unit causes the display unit to display the plurality of anterior eye part images.

5. The apparatus according to claim 1, further comprising:
    a blowing unit configured to blow compressed air against a cornea of the eye to deform the cornea; and
    a detection unit configured to detect a corneal deformation signal indicating a state in which the cornea is deformed by the compressed air, by projecting measurement light onto the cornea,
    wherein said measuring unit measures an eye pressure value of the eye, as the unique information, from the corneal deformation signal detected by said detection unit.

6. The apparatus according to claim 3, further comprising a second determination unit configured to calculate a shift amount of said measuring unit relative to a measurement optical axis from the anterior eye part image and determine whether the shift amount exceeds a predetermined threshold,
    wherein when the plurality of pieces of unique information vary relative to the average value calculated by said calculation unit, and said second determination unit determines that the shift amount exceeds a predetermined threshold, said display control unit causes the display unit to display a combination of the anterior eye part image and a shift amount relative to the measurement optical axis, based on a plurality of times of measurement.

7. The apparatus according to claim 1, further comprising:
    an alignment state detection unit configured to detect an alignment state between an eye to be examined of an object and said measuring unit; and
    an alignment unit configured to position said measuring unit to the eye from a detection result obtained by said alignment state detection unit.

8. The apparatus according to claim 1, further comprising a selection acceptance unit configured to accept selection of one piece of unique information of the plurality of pieces of unique information based on the plurality of anterior eye part images displayed on the display unit.

9. The apparatus according to claim 8, further comprising:
    a determination unit configured to determine whether each of the plurality of pieces of unique information satisfies a condition as a criterion indicating reliability, wherein said calculation unit calculates an average value of the plurality of pieces of unique information determined by said determination unit as satisfying the condition, and calculates variations of the plurality of pieces of unique information relative to the average value;

a blowing unit configured to blow compressed air against a cornea of the eye to deform the cornea;

a detection unit configured to detect a corneal deformation signal indicating a state in which the cornea is deformed by the compressed air, by projecting measurement light onto the cornea, wherein said measuring unit measures an eye pressure value of the eye, as the unique information, from the corneal deformation signal detected by said detection unit;

an alignment state detection unit configured to detect an alignment state between an eye to be examined of an object and said measuring unit;

an alignment unit configured to position said measuring unit to the eye from a detection result obtained by said alignment state detection unit; and a control unit configured to control operations of said imaging unit, said blowing unit, said detection unit, and said measuring unit after completion of operation of said alignment state detection unit, operation of said alignment unit, and positioning operation of said alignment unit, wherein when said control unit accepts an operation instruction to measure an eye pressure of one eye to be examined, of one eye and the other eye of an object as eyes to be examined, first and then consecutively measure an eye pressure of the other eye, if said determination unit determines that at least one piece of unique information, of a plurality of pieces of unique information measured by a plurality of times of measurement on one eye to be examined satisfies the condition, and variations of the plurality of pieces of unique information relative to the average value calculated by said calculation unit satisfy the condition, said control unit interrupts measurement of an eye pressure of the other eye to be examined, the display unit displays a combination of the anterior eye part image and the unique information stored in said storage unit as measurement results corresponding to a plurality of times of measurement on said one eye to be examined, and said control unit resumes the interrupted measurement of the eye pressure of the other eye to be examined after accepting selection of one measurement result selected from the measurement results corresponding to the plurality of times of measurement via said selection acceptance unit.

10. The apparatus according to claim 1, wherein said display control unit causes the display unit to further display unique information of the eye to be examined measured by said measuring unit and the corneal deformation signal detected by said detection unit.

11. The apparatus according to claim 6, wherein a shift amount relative to the measurement optical axis of said measuring unit includes a shift amount between a cornea center and the measurement optical axis and a shift amount between a pupil center and the measurement optical axis.

12. A non-transitory computer-readable storage medium storing a program, wherein the program is configured to cause a computer to function as an ophthalmic apparatus, the ophthalmic apparatus comprising (a) an imaging unit configured to capture an anterior eye part image of an eye to be examined, (b) a measuring unit configured to measure unique information of the eye, (c) a calculation unit configured to calculate variations of a plurality of pieces of unique information measured by said measuring unit, and (d) a display control unit configured to cause a display unit to display a plurality of anterior eye part images respectively corresponding to the plurality of pieces of unique information when variations calculated by said calculation unit satisfy a predetermined condition.

13. The apparatus according to claim 2, further comprising:

a blowing unit configured to blow compressed air against a cornea of the eye to deform the cornea; and a detection unit configured to detect a corneal deformation signal indicating a state in which the cornea is deformed by the compressed air, by projecting measurement light onto the cornea, wherein said measuring unit measures an eye pressure value of the eye, as the unique information, from the corneal deformation signal detected by said detection unit.

14. The apparatus according to claim 13, wherein said display control unit causes the display unit to further display (a) unique information of the eye to be examined measured by said measuring unit and (b) the corneal deformation signal detected by said detection unit.

15. The apparatus according to claim 7, further comprising a selection acceptance unit configured to accept selection of one piece of unique information of the plurality of pieces of unique information based on the plurality of anterior eye part images displayed on the display unit.

16. The apparatus according to claim 14, further comprising a selection acceptance unit configured to accept selection of one piece of unique information of the plurality of pieces of unique information based on the plurality of anterior eye part images displayed on the display unit.

17. The apparatus according to claim 1, wherein said display control unit causes the display unit not to display the plurality of anterior eye part images when variations calculated by said calculation unit do not satisfy the predetermined condition.

18. The apparatus according to claim 1, wherein said calculation unit calculates an average value of the plurality of pieces of unique information, and calculates variations of the plurality of pieces of unique information relative to the average value.

19. The apparatus according to claim 1, wherein said calculation unit calculates an average value of the plurality of pieces of unique information, and calculates variations of the plurality of pieces of unique information relative to the average value, and wherein the display control unit causes the display unit to display the plurality of anterior eye part images respectively corresponding to the plurality of pieces of unique information when there are the same variations among the variations calculated by said calculation unit.

20. The apparatus according to claim 14, wherein said calculation unit calculates an average value of the plurality of pieces of unique information, and calculates variations of the plurality of pieces of unique information relative to the average value, and wherein the display control unit causes the display unit to display the plurality of anterior eye part images respectively corresponding to the plurality of pieces of unique information when there are the same variations among the variations calculated by said calculation unit.

* * * * *